United States Patent [19]

Kelder et al.

[11] Patent Number: 4,701,450

[45] Date of Patent: Oct. 20, 1987

[54] STEROIDS FOR USE AS IMMUNOMODULATORS

[75] Inventors: Jan Kelder; Hermanus A. M. Verheul, both of Oss, Netherlands

[73] Assignee: Akzo N.V., Arnhem, Netherlands

[21] Appl. No.: 712,438

[22] Filed: Mar. 18, 1985

[30] Foreign Application Priority Data

Mar. 21, 1984 [NL] Netherlands .................. 8400888

[51] Int. Cl.[4] ........................................ A61K 31/56
[52] U.S. Cl. ................................ 514/177; 514/178; 514/180; 514/182
[58] Field of Search ............... 514/177, 180, 178, 182

[56] References Cited

U.S. PATENT DOCUMENTS

| 3,012,045 | 12/1961 | Colton et al. | 260/397.4 |
| 3,301,879 | 1/1967 | Wettstein et al. | 260/397.5 |
| 4,412,993 | 11/1983 | Sokolowski | 424/243 |
| 4,546,098 | 10/1985 | Fishman | 260/397.3 |

FOREIGN PATENT DOCUMENTS

| 1543273 | 8/1969 | Fed. Rep. of Germany | 514/178 |
| 1583441 | 10/1969 | France | 514/178 |
| 2034509 | 12/1970 | France | 514/178 |
| 884412 | 12/1961 | United Kingdom | 514/178 |
| 885782 | 12/1961 | United Kingdom | 514/178 |
| 931009 | 7/1963 | United Kingdom | 514/178 |
| 941634 | 11/1963 | United Kingdom | 514/178 |
| 1107553 | 3/1968 | United Kingdom | 260/397.45 |

OTHER PUBLICATIONS

Espey; Biology of Reproduction, vol. 22 (1980), pp. 73–106, Ovulation as an Inflammatory Reaction—A Hypothesis.
Chem. ABS. 95:181256T (1981).
Chem. ABS. 1977–1981, Chem. Substance Index, 35111CS.

Primary Examiner—Leonard Schenkman
Assistant Examiner—Joseph A. Lipovsky
Attorney, Agent, or Firm—Wegner & Bretschneider

[57] ABSTRACT

The invention relates to a group of $\Delta^4$- and $\Delta^{5(10)}$-oestrene derivatives having an alkyl(1–4 C) substituent in position 6 or 7, an oxy substituent in position $17\beta$ and optionally an oxo- or oxy-substituent in position 3 and a hydrocarbyl(1–4 C) group in position $17\alpha$, for use as immunomodulator. The compounds are in particular suitable for therapeutic use in the treatment of autoimmune diseases.

18 Claims, No Drawings

STEROIDS FOR USE AS IMMUNOMODULATORS

The invention relates to steroids of the oestrane series, in particular $\Delta^4$- and $\Delta^{5(10)}$-oestrene derivatives having an alkyl substituent in position 6 or 7, for use as immunomodulators, and to pharmaceutical preparations which contain these steroids as the active constituent. The invention also relates to prophylactic and therapeutic methods of treating auto-immune diseases in mannals.

Oestrene derivatives having a double bond between carbon atoms 4 and 5 or 5 and 10 and an alkyl substituent in position 6 or 7 are known. See, for example, British Pat. Nos. 884 412, 885 782, 919 575, 931 009, 941 634, 965 292, 1 087 598, 1 104 462, 1 107 553 and 1 292 201, U.S. Pat. Nos. 2,891,078, 3,012,045, 3,301,879, 3,341,557, 3,515,719 and 4,412,993, Netherlands Patent Applications Nos. 300 903 and 68.03 328 and Japanese Published Patent Application 21 373/63 (Dw 9532F).

Of the oestrene derivatives described in the literature, to which the present patent application relates, it is reported that they possess hormonal properties, in particular androgenic, anabolic, oestrogenic, progestative and/or ovulation-inhibiting properties.

Surprisingly, it has now been found that a certain group of $\Delta^4$- and $\Delta^{5(10)}$-oestrene derivatives having an alkyl substituent in position 6 or 7 possesses immunomodulating properties. The present invention therefore relates to oestrene derivatives having the general formula I

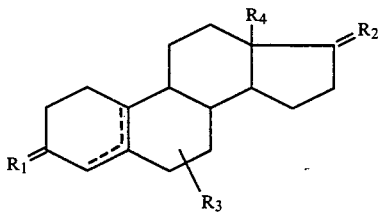

wherein
$R_1 = H_2$, $H(OR_5)$ or $O$;
$R_2 = (\alpha R_6)(\beta OR_7)$;
$R_3 =$ alkyl(1-4 C) in position 6 or 7;
$R_4 =$ alkyl(1-4 C);
$R_5 =$ H or acyl(1-18 C);
$R_6 =$ H or hydrocarbyl(1-4 C);
$R_7 =$ H or acyl(1-18 C); and
the broken lines indicate the presence of a double bond in the 4,5- or 5,10-position,
for use as immunomodulators.

The invention also relates to pharmaceutical preparations having immunomodulating properties, which preparations contain at least one of the compounds having the formula I.

By alkyl(1-4 C) there is meant methyl, ethyl, propyl, isopropyl, butyl, isobutyl or t-butyl. $R_3$ is preferably methyl and moreover is preferably located in the $\alpha$-position. $R_4$ is preferably methyl.

Acyl(1-18 C) is, as the affix (1-18 C) already indicates, derived from an organic carboxylic acid having 1-18 carbon atoms. As examples thereof there may be mentioned: formic acid, acetic acid, propionic acid, butyric acid, isobutyric acid, trimethylacetic acid, valeric acid, caproic acid, capric acid, pelargonic acid, undecylenic acid, lauric acid, palmitic acid, oleic acid, phenylacetic acid, phenylpropionic acid, cyclopentylpropionic acid, cyclohexylcarboxylic acid, cyclooctylacetic acid, benzoic acid, fumaric acid, maleic acid, succinic acid and citric acid.

By hydrocarbyl(1-4 C) there is meant one of the groups referred to above as alkyl(1-4 C) or an unsaturated version thereof, having 2-4 carbon atoms, such as vinyl, ethynyl, allyl, propargyl, isopropenyl, butynyl or butadienyl.

$R_6$ is preferably ethynyl, with $R_7$ then preferably being H.

The compounds having the formula I and the pharmaceutical preparations based thereon have, as stated, immunomodulating properties, that is to say they are capable of exerting a favourable influence on the immune system in mammals. They are in particular suitable for therapeutic use in the treatment of auto-immune diseases, such as SLE (systemic lupus erythematosus), rheumatoid arthritis, auto-immune thyroiditis, Sjøgren's syndrome, idiopathic thrombocytopenic purpura and haemolytic anaemia. The compounds can also be used prophylactically. They can be delivered orally, rectally, parenterally or locally (topically or sublingually), usually in combination with a carrier and other pharmaceutical auxiliaries.

The compounds to be used in the present invention are known from the abovementioned patent specifications or can be prepared in a manner similar to that described in the said patent specifications.

Examples of steroids having the formula I, which may be used according to the invention, are: 7$\alpha$-methyl-17$\alpha$-ethinyl-17$\beta$-hydroxy-$\Delta^{5(10)}$-oestren-3-one, 7$\alpha$-methyl-17$\alpha$-ethinyl-$\Delta^{5(10)}$-oestren-17$\beta$-ol, 7$\alpha$-methyl-17$\alpha$-ethinyl-17$\beta$-hydroxy-$\Delta^4$-oestren-3-one, 7$\alpha$-methyl-17$\alpha$-ethyl-17$\beta$-hydroxy-$\Delta^{5(10)}$-oestren-3-one, 7$\alpha$-methyl-17$\alpha$-ethinyl-$\Delta^{5(10)}$-oestrene-3$\alpha$,17$\beta$-diol, 7$\alpha$-methyl-17$\alpha$-ethinyl-$\Delta^{5(10)}$-oestrene-3$\beta$,17$\beta$-diol, 7$\alpha$-methyl-17$\alpha$-allyl-17$\beta$-hydroxy-$\Delta^{5(10)}$-oestren-3-one, 7$\alpha$,17$\alpha$-dimethyl-17$\beta$-hydroxy-$\Delta^4$-oestren-3-one, 7$\alpha$-methyl-17$\alpha$-ethinyl-$\Delta^4$-oestrene-3$\beta$,17$\beta$-diol, 6$\alpha$-methyl-17$\beta$-hydroxy-$\Delta^4$-oestren-3-one, 6$\beta$-methyl-17$\beta$-hydroxy-$\Delta^4$-oestren-3-one, 6$\alpha$-methyl-17$\alpha$-ethinyl-17$\beta$-hydroxy-$\Delta^4$-oestren-3-one, 6$\alpha$-methyl-17$\alpha$-ethyl-17$\beta$-hydroxy-$\Delta^4$-oestren-3-one, 6$\alpha$-methyl-17$\alpha$-ethinyl-$\Delta^4$-oestren-17$\beta$-ol, 6$\alpha$-methyl-17$\alpha$-ethinyl-17$\beta$-hydroxy-$\Delta^{5(10)}$-oestren-3-one, 6$\alpha$-methyl-17$\alpha$-allyl-17$\beta$-hydroxy-$\Delta^{5(10)}$-oestren-3-one and esters thereof. Particularly effective are the compounds 7$\alpha$-methyl-17$\alpha$-ethinyl-17$\beta$-hydroxy-$\Delta^{5(10)}$-oestren-3-one (tibolone) and the corresponding 17$\alpha$-ethyl compound.

The pharmaceutical preparations for use according to the invention can be prepared in accordance with known galenical techniques, for example by converting the relevant steroid compound having the formula I into a form which is suitable for enteral (for example oral or rectal), parenteral (e.g. intravenous, subcutaneous or intramuscular) or local (via the skin or mucous membranes) administration. For this purpose, the steroid compound is mixed with or dissolved in a pharmaceutically acceptable carrier.

Examples of such preparations are tablets, pills, treats, coated tablets, pastilles, suppositories, powders, (micro-)capsules, emulsions, suspensions, solutions, implants, ointments, creams and lotions.

The quantity of active compound ($\Delta^4$- or $\Delta^{5(10)}$-oestrene derivative according to formula I) in the preparations to be administered enternally is 0.01–25.0 mg and usually 0.1–5.0 mg. The daily dose is usually 1–3 dosage units. In the liquid and semi-soft dosage forms which are injected or are applied to the skin or mucous membranes, the concentration of active compound is approximately 0.005 to 20% by weight, usually 0.01 to 5% by weight. Injections are usually carried out with dosage units of 1 ml.

The pharmaceutically acceptable carriers can be composed of one or more of the following ingredients: starch (for example potato starch or corn starch), sugars (for example lactose), lubricants (magnesium stearate or stearic acid), binders (for example amylopectin or polyvinylpyrrolidone), water, alcohol, glycerol and derivatives thereof, vegetable, animal and mineral oils and fats, fatty alcohols, silicones, lanolins, polyalkylene glycols, cellulose derivatives, silica, dispersants, emulsifiers, surfactants, antioxidants preservatives, etc.

The immuno-modulating properties of compounds according to formula I are revealed by means of a test which is representative of the said action, namely the Bursa model.

In this model, the effect of the compound to be investigated on the development of the Fabricius bursa is investigated in chicks. The compound is administered in the embryonic stage by dipping eggs which have been incubated for three days in an ethanol solution of the compound to be investigated. The eggs are thereafter incubated further and ten days after the eggs have hatched, the chicks are killed and the body weight and weight of the Fabricius bursa are determined. The Fabricius bursa is an organ which is located immediately next to the cloaca and is responsible for the maturing of the B-cell system, which ensures the production of antibodies. The inhibiting action of the compound to be investigated on the development of the said organ is determined, using nandrolone (19-nor-testosterone) as reference.

The use of nandrolone as reference is based on the fact that nandrolone, in another model, the so-called NZB/W model, has an advantageous effect on lupus in NZB/W mice (murine lupus), which is an indication of an advantageous effect of this compound on auto-immune diseases. See, in this context, Clin. Exp. Immunol. 44 (1981), pages 11-17, in which article a comparison is made between the effect of testosterone and nandrolone in the NZB/W model, the conclusion being that the advantageous effect on "murine lupus" does not show any correlation with the hormonal action, namely with the androgenic action in the case in question.

A difficulty of the NZB/W model is that the tests in this model require such a long time (1 to 1½ years). For screening a large number of compounds, the Bursa model is to be preferred.

The results of the tests in the Bursa model are summarised in the folowing table.

| Compound | P |
|---|---|
| 7α-methyl-17α-ethinyl-17β-hydroxy-$\Delta^{5(10)}$-oestren-3-one | 250 |
| 7α-methyl-17α-ethyl-17β-hydroxy-$\Delta^{5(10)}$-oestren-3-one | 660 |
| 7α-methyl-17α-ethinyl-$\Delta^{5(10)}$-oestrene-3α,17β-diol | 20 |
| 7α-methyl-17α-ethinyl $\Delta^{5(10)}$-oestrene-3β,17β-diol | 26 |
| 7α-methyl-17α-ethinyl-17β-hydroxy-$\Delta^4$-oestren-3-one | 120 |
| 6α-methyl-17α-ethinyl-17β-hydroxy-$\Delta^{5(10)}$-oestren-3-one | 60 |

-continued

| Compound | P |
|---|---|
| 6α-methyl-17α-ethinyl-17β-hydroxy-$\Delta^4$-oestren-3-one | 25 |
| 6α-methyl-17α-ethyl-17β-hydroxy-$\Delta^4$-oestren-3-one | 150 |
| 6α-methyl-17α-ethinyl-$\Delta^4$-oestren-17β-ol | 89 |
| 6α-methyl-17β-hydroxy-$\Delta^4$-oestren-3-one | 15 |
| nandrolone (reference) | 1 |

Column P indicates the potency of the compound in comparison with that of nandrolone. The values found appear not to correlate with the endocrinological activities of these compounds.

The effect of the compound 7α-methyl-17α-ethinyl-17β-hydroxy-$\Delta^{5(10)}$-oestren-3-one (tibolone) was studied extensively in the NZB/W mouse model. NZB/W F-1 hybrid mice spontaneously develop an auto-immune disease with symptoms resembling those of human SLE and also develop Sjøgren's syndrome-like disorders in the salivary and lacrimal glands. Tibolone inhibited significantly the expression of SLE and Sjøgren's syndrome-like disorders in the NZB/W mice. For instance, mortality was reduced significantly. The median survival of female mice increased from 40 weeks (placebo) to 68 weeks with a dose of 0.1 mg/mouse/day and of castrated male mice from 54 weeks (placebo) to 74 weeks. The same dose significantly delayed the development of proteinuria. Also, the mononuclear cell infiltrations in the submandibular glands, expressed as the so-called infiltration index, were reduced from about 55 to below 10 in 39 weeks old NZB/W mice. Further, tibolone caused significant reduction of the auto-antibody (anti-dsDNA) levels in the serum of these mice.

The invention is further illustrated by the examples which follow. In each of the examples, the active compound can, if desired, be replaced by an equivalent quantity of another compound within the scope of formula I.

EXAMPLE 1

Tablets

| | | |
|---|---|---|
| (a) | 7α-methyl-17α-ethinyl-17β-hydroxy-$\Delta^{5(10)}$-oestren-3-one | 2.5 mg |
| | potato starch | 10.0 mg |
| | magnesium stearate | 0.5 mg |
| | ascorbyl palmitate | 0.2 mg |
| | amylopectin | 2.0 mg |
| | lactose to make up to | 100.0 mg |
| (b) | 7α-methyl-17α-ethyl-17β-hydroxy-$\Delta^{5(10)}$-oestren-3-one | 2.0 mg |
| | corn starch | 10.0 mg |
| | stearic acid | 1.0 mg |
| | silica ("Aerosil") | 1.0 mg |
| | polyvinylpyrrolidone | 3.0 mg |
| | dl-α-tocopherol | 0.1 mg |
| | lactose to make up to | 100.0 mg |
| (c) | 7α-methyl-17α-ethinyl-17β-hydroxy-α4-oestren-3-one | 5.0 mg |
| | potato starch | 25.0 mg |
| | magnesium stearate | 4.0 mg |
| | dl-α-tocopherol | 0.2 mg |
| | lactose to make up to | 100.0 mg |

EXAMPLE II

Injection preparations

| (a) Suspension | |
|---|---|
| 6α-methyl-17α-ethyl-17β-hydroxy-Δ⁴-oestren-3-one | 1.0 mg |
| Na carboxymethylcellulose | 5.0 mg |
| sodium bisulphite | 0.2 mg |
| water to make up to | 1.0 ml |
| (b) Oil solution | |
| 6α-methyl-17α-ethinyl-Δ⁴-oestren-17β-ol | 2.0 mg |
| BHA/BTA (1/1) | 0.2 mg |
| groundnut oil to make up to | 1.0 ml |

We claim:

1. A method of treating auto-immune diseases in mammals suffering from auto-immune diseases, which comprises administering to the mammal a non-toxic, therapeutically effective amount of a steroid compound of the oestrane series, having the general formula

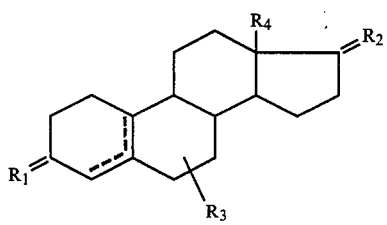

wherein
$R_1 = H_2$, $H(OR_5)$ or $O$;
$R_2 = (\alpha R_6)(\beta OR_7)$;
$R_3$ = alkyl(1–4 C) in position 6 or 7;
$R_4$ = alkyl(1–4 C);
$R_5$ = H or acyl(1–18 C);
$R_6$ = H or hydrocarbyl(1–4 C);
$R_7$ = H or acyl(1–18 C); and
the broken lines indicate the presence of a double bond in the 4,5- or 5,10-position.

2. The method of claim 1, wherein $R_1 = O$ and $R_4$ = methyl.

3. A method of claim 1, wherein the auto-immune disease is systemic lupus ertyhematsosus, rhematoid arthritis, auto-immune thyroiditis, Sjøgren's syndrome, idiopathic thrombocytopenic purpura or haemolytic anaemia.

4. The method of claim 3, wherein $R_3$ and $R_4$ both are methyl.

5. The method of claim 3, wherein $R_3 = \alpha$-methyl and $R_4$ = methyl.

6. The method of claim 3, wherein $R_4$ = methyl, $R_6$ = ethynyl and $R_7$ = H.

7. The method of claim 3, wherein $R_1 = O$, $R_3 = 7\alpha$-methyl, $R_4$ = methyl, $R_6$ = ethynyl or ethyl and $R_7$ = H.

8. The method of claim 7, wherein the double bond is in 5,10-position.

9. The method of claim 3, wherein the daily dosage is 0.01 to 200 mg.

10. The method of claim 9, wherein the daily dosage is 0.1 to 50 mg.

11. The method of claim 3, wherein the steroid is administered in admixture with a pharmaceutically acceptable carrier.

12. A method for the prevention of auto-immune diseases in mammals being susceptible to said diseases which comprises administering to the mammal a non-toxic, therapeutically effective amount of a steroid compound of the oestrane series, having the general formula

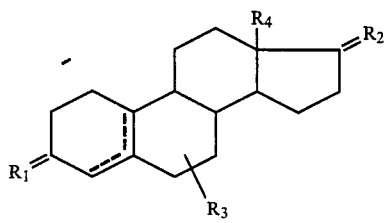

wherein
$R_1 = H_2$, $H(OR_5)$ or $O$;
$R_2 = (\alpha R_6)(\beta OR_7)$;
$R_3$ = alkyl(1–4 C) in position 6 or 7;
$R_4$ = alkyl(1–4 C);
$R_5$ = H or acyl(1–18 C);
$R_6$ = H or hydrocarbyl(1–4 C);
$R_7$ = H or acyl(1–18 C); and
the broken lines indicate the presence of a double bond in the 4,5- or 5,10-position.

13. A method of claim 12, wherein the auto-immune disease is systemic lupus ertyhematsosus, rhematoid arthritis, auto-immune thyroiditis, Sjøgren's syndrome, idiopathic thrombocytopenic purpura or haemolytic anaemia.

14. The method of claim 13, wherein $R_1 = O$, $R_3 = 7\alpha$-methyl, $R_4$ = methyl, $R_6$ = ethynyl or ethyl and $R_7$ = H.

15. The method of claim 14, wherein the double bond is in 5,10-position.

16. The method of claim 13, wherein the daily dosage is 0.01–200 mg.

17. The method of claim 16, wherein the daily dosage is 0.1–50 mg.

18. The method of claim 13, wherein the steroid is administered in admixture with a pharmaceutically acceptable carrier.

* * * * *